United States Patent [19]

Affonso

[11] 4,370,305
[45] Jan. 25, 1983

[54] DEVICE FOR THE STERILIZATION OF FLUID SUBSTANCES

[75] Inventor: Alvaro Affonso, Bad Homburg von der Hohe, Fed. Rep. of Germany

[73] Assignee: Hoelzle & Chelius KG, Neu-Isenburg, Fed. Rep. of Germany

[21] Appl. No.: 170,104

[22] Filed: Jul. 18, 1980

[30] Foreign Application Priority Data

Jul. 23, 1979 [DE] Fed. Rep. of Germany ....... 2929813

[51] Int. Cl.³ .................................................. A61L 2/20
[52] U.S. Cl. ......................................... 422/292; 210/192;
210/205; 210/753; 210/754; 210/757; 210/764;
239/34; 422/29; 422/37; 422/305
[58] Field of Search ............... 422/29, 37, 238, 239,
422/305, 292; 210/753, 754, 757, 764, 192, 205;
239/34

[56] References Cited

U.S. PATENT DOCUMENTS

| | | | |
|---|---|---|---|
| 1,581,115 | 4/1926 | Harold | 422/37 X |
| 3,183,057 | 5/1965 | Marks et al. | 422/29 |
| 3,412,935 | 11/1968 | O'Keefe | 239/34 |
| 3,468,796 | 9/1969 | Noll et al. | 210/754 X |
| 3,488,420 | 1/1970 | Keast et al. | 422/29 X |
| 3,768,104 | 10/1973 | Sanderson | 422/29 X |
| 3,792,978 | 2/1974 | Freedman | 422/48 |
| 3,856,932 | 12/1974 | May | 422/37 X |
| 3,862,031 | 1/1975 | Leonard | 422/48 X |
| 4,128,397 | 12/1978 | Lynch | 422/29 |

*Primary Examiner*—Barry S. Richman
*Attorney, Agent, or Firm*—Schwartz, Jeffery, Schwaab, Mack, Blumenthal & Koch

[57] ABSTRACT

A device for the sterilization of fluids wherein a sterilizing gas is chemically generated in-situ within a liquid-impermeable container, which container is in contact with the fluid to be sterilized. The container is constructed at least in part of a solid, non-porous, liquid-impermeable synthetic plastic barrier, which barrier permits controlled diffusion of the sterilizing gas therethrough while preventing passage therethrough of impurities and the residue of the gas generation reaction.

14 Claims, 11 Drawing Figures

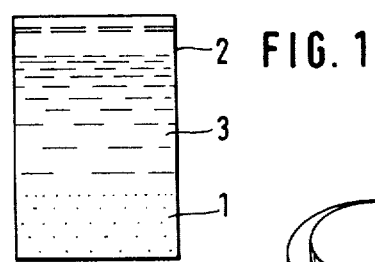
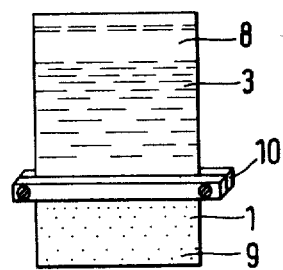
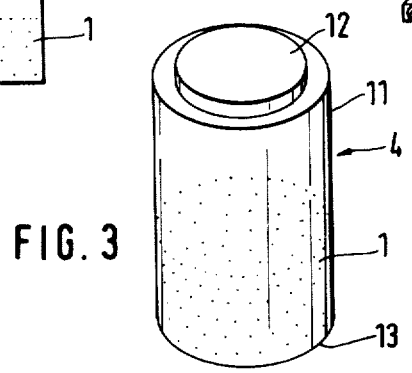
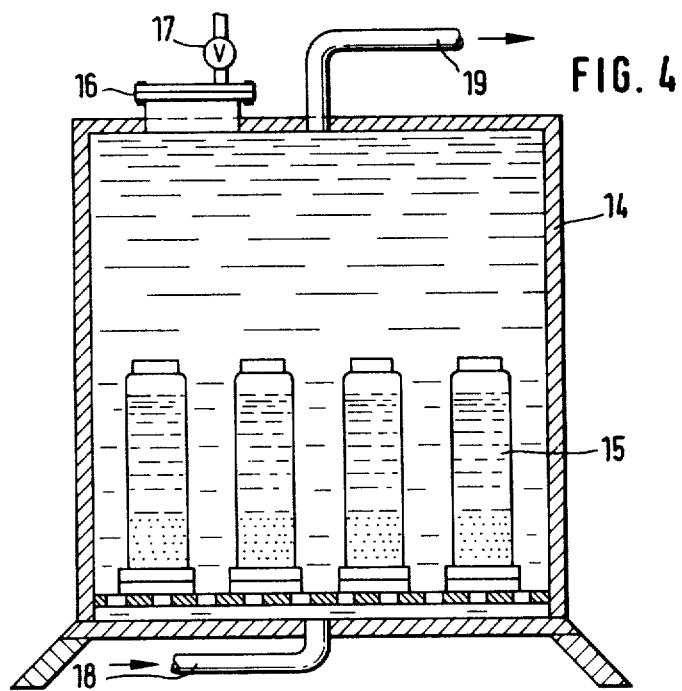

DEVICE FOR THE STERILIZATION OF FLUID SUBSTANCES

BACKGROUND OF THE INVENTION

1. Field of the Invention

The invention concerns a device for the sterilization of fluid substances. More particularly, the invention relates to the sterilization of water or air, with the aid of a substance that develops a gas, having a disinfecting effect, upon the addition of an activator, preferably an aqueous solution.

2. Background of the Prior Art

In the field of the sterilization of medical instruments or, for example, in the preservation of food items, it is known to use synthetic plastic sheets that are permeable for gaseous substances. It is, therefore, important, particularly in the packaging of food items, to reduce the diffusion of oxygen in the direction of the food and the diffusion of carbon dioxide and aromatic gases from the packaged food items into the atmosphere. The diffusion of gases and of aromatic substances through synthetic plastic sheets is affected by numerous factors, the most important of which are the nature of the gases, the temperature and the pressure and the properties of the synthetic plastic sheet.

The diffusion of gases through synthetic plastic sheets may be interpreted in a manner similar to the diffusion of liquids, i.e. the gas is dissolved in the plastic material, migrates through it and emerges finally on the other side as the gas, whereupon it may enter in solution with a medium existing on that side.

Aroma tightness, which is highly important in relation to packaging technology, does not parallel the sealing properties of the sheet with respect to gases and is strongly dependent on the chemical structure of the aromatic substance. In the case of sheets which absorb humidity, such as for example, cellophane and polyamide, diffusion is accelerated by higher degrees of humidity. Diffusibility does not depend on the thickness of the sheet, but exclusively on the material. The thickness of the sheet merely represents a time factor, but has a strong influence on diffusion values.

The sterilization of drinking water or water in bathing facilities, at the present time, is effected overwhelmingly by means of chlorine gas from gas bottles. The production of chlorine gas, the filling of the gas into bottles, the transportation, storage and discharge during sterilization are all expensive and potentially dangerous steps. Thus, they are normally handled by skilled persons only, and such handling is complicated. Accordingly, extremely accurate dosages must be maintained particularly during sterilization in order to prevent danger to persons. In view of this fact, attempts have already been made to use chlorine gas producing substances. However, the application of substances of this type has the significant disadvantage that following the release of the gas, the residues of the chemical compounds remain in the water to be sterilized so that undesirable or even toxic effects cannot be excluded with certainty. This means that, for example, in the sterilization of water in swimming pools, persons swimming therein may come into contact with such residues, whereby even internal contacts cannot be excluded.

Since the substances releasing the gas are produced industrially, they may contain impurities. Therefore, even when the main residue remaining is harmless, detrimental or undesirable, contamination may take place from impurities as the products are not prepared in an analytically pure manner.

West German Offenlegungsschrift No. 17 67 635 discloses a chlorine filter, which is intended specifically for swimming pools. Therein the chlorine tablets or chlorine granules are first packaged in the proper doses in a synthetic plastic bag which is perforated over its surface or part of its surface. For transportation or storage of the chlorine tablets, this perforated plastic bag is packed in a second synthetic plastic bag and sealed in an absolutely tight manner, so that no chlorine gas may escape. Plastic bags provided with perforations, however, are incapable of retaining impurities of the chlorine gas releasing substances.

West German Offenlegungsschrift No. 16 42 474 further discloses a process and a device for the regeneration of water with gaseous media, wherein the gas, for example carbon dioxide, is to be mixed with the liquid by means of diffusion. The process is realized by means of an apparatus consisting of a container to be partially filled with gas and intended to establish direct contact between the gas and the liquid, thus creating favorable conditions for diffusion. In order to restrict the diffusion to a certain level and to maintain a constant supply of the gas in the container, partitions or sleeves permeable to the gas are provided. These means therefore serve to slow the mixing process in order to maintain a continuous action. The diffusion process in the above Offenlegungsschrift does not take place as described across plastic membranes but during free contact between gas and water.

SUMMARY OF THE INVENTION

It is an object of the present invention to provide an apparatus for the sterilization of fluid substances, particularly of water or air, whereby a disinfecting gas is produced from a substance, the residue of which including its impurities, are maintained separate from the medium to be disinfected.

It is a further object of the invention to provide a source of gas which operates continuously under normal conditions, for example at room temperature and normal atmospheric pressure. At the same time control of the release of gas is made possible.

The objects and advantages of the present invention are attained by means of the above-mentioned apparatus wherein the gas producing substance is in a container having at least one sidewall of a synthetic, plastic sheet through which the gas may diffuse. The sheet also serves to retain the residue of the gas producing substance, including its impurities. At least one side wall having the plastic sheet is in contact on the outside with the fluid medium to be disinfected.

In a further development of the invention, the gas-releasing and disinfecting substance actuated by the addition of an activator is contained in a bag, flexible tube or cartridge made of a synthetic plastic material, wherein the bag, flexible tube or cartridge is provided with a means for the introduction of the activator and the bag or bags, tube or tubes and cartridge or cartridges are arranged in a vessel through which the medium to be sterilized is flowing.

According to the invention, polyethylene sheets, soft or hard (PE), polypropylene (PP), polyvinylchloride (PVC), soft PVC, polyethylenepolypropylenepolyamide, polytetrafluoroethylene, sheets or copolymers and/or derivatives of these groups may be used as the synthetic plastic sheet.

The disinfecting gas preferably consists of a halogen, its gaseous derivatives or compounds (for example its oxides) and of sulfur dioxide.

In a further development of the invention the container, bag, flexible tube or cartridge may comprise of two chambers wherein one chamber contains the gas source and the other chamber contains the activator. The chambers are separated from each other by a releasable partitioning device.

One advantage of the device of the invention is the use of a gas releasing substance produced inexpensively in an industrial process. That is, it is now possible to use a substance that is not analytically pure and which may leave a residue with undesirable or toxic properties without contaminating the fluid undergoing sterilization.

In one embodiment of the invention, the medium to be sterilized flows along the side of the sheet surface through which the disinfecting gas is diffusing, so that the gas is being continuously removed. In this manner, it is feasible to continuously maintain a chemical inequilibrium in the direction of the release of the gas. The production of the gas may be controlled in addition to the introduction of a certain activator, by the flow rate of the medium to be disinfected.

In a further development of the invention, it is equally possible to pass the substance developing the disinfecting gas continuously through an exchanger apparatus. Herein, the substance providing the disinfecting gas may be located in a storage container which is connected to the exchange apparatus. In order to actuate the chemical reaction, a fluid like for example water having a definite pH is fed into the storage container. The flow rate of the feed to the exchanger is controlled so that the substance supplying the gas will release the disinfecting gas almost completely, when it leaves the exchanger.

BRIEF DESCRIPTION OF THE DRAWINGS

The invention shall be explained in more detail hereinafter with the aid of a drawing. In the drawing:

FIG. 1 shows an air- and water-tight sealed polyethylene bag;

FIG. 2 demonstrates a bag similar to that of FIG. 1 but with separate chambers;

FIG. 3 shows a metering cartridge with a tightly sealable filling orifice;

FIG. 4 illustrates a stright-through metering container;

DETAILED DESCRIPTION OF THE PREFERRED EMBODIMENT

Figure 5:
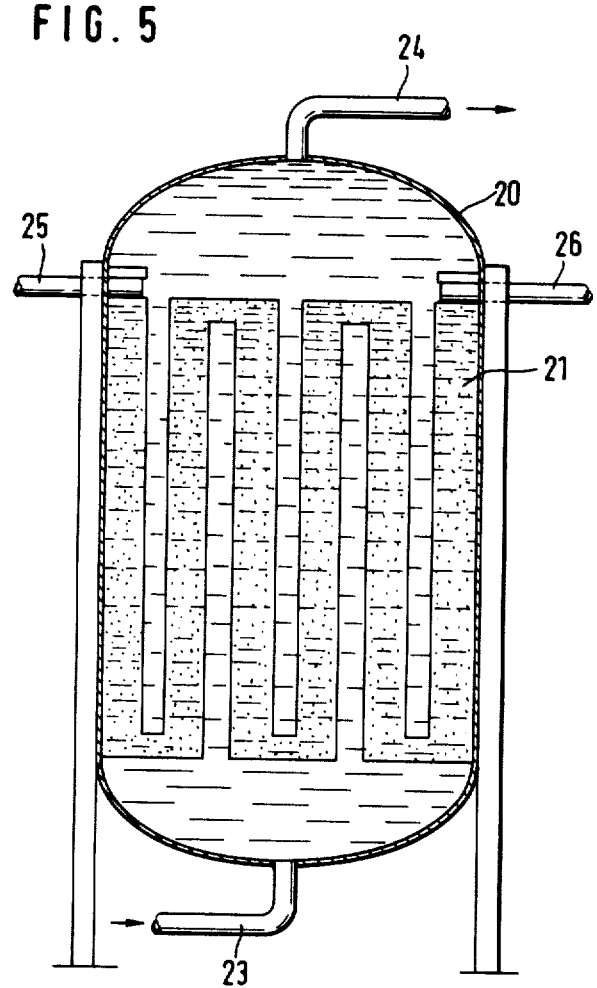
FIG. 5 depicts a further variant of a straight-through metering device.

FIG. 1 shows a polyethylene bag 2 which is welded air and water tight and which contains the substance 1, releasing the disinfecting gas. The substance 1 may consist, for example, of the sodium salt of dichlorisocyanuric acid with the chemical formula of $C_3N_3O_3Cl_2Na$. It further contains the activator 3 which is a liquid with a predetermined pH value.

The ability of this and other chlorinated isocyanuric acids to produce disinfecting effects is actuated by means of the release of active chlorine gases upon the addition of water. The hydrolysis results in the formation of isocyanuric acid.

Both organic and inorganic substances capable of cleaving off chlorine may be used. Suitable organic chlorine releasing substances are chloramine B (benzenesulfochloramine-Na), chloramine T, which develops nascent oxygen in water. Halazone (p-dichlorosulfamylbenzoic acid) may be used to disinfect drinking water.

As an inorganic halogen donor, for example, sodium chlorite may be used, which in acid media like for example with the aid of amido-sulfonic acid develops chlorine dioxide according to the following equation:

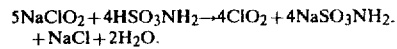

$$5NaClO_2 + 4HSO_3NH_2 \rightarrow 4ClO_2 + 4NaSO_3NH_2 + NaCl + 2H_2O.$$

FIG. 2 shows a bag similar to that of FIG. 1 comprising two chambers 8 and 9, separated by a releasable separating device 10. The upper chamber 8 contains the activator 3 and the lower chamber 9 the gas donor 1. The releasable separating device 10 in this embodiment comprises a clip, which when released, allows contact of the activator with the gas donor. Immediately after this, the corresponding gas is generated, which in turn diffuses outwardly through the bag.

FIG. 3 shows a metering cartridge 4 with a filling orifice that may be sealed tightly. The sheathing 11 of the cartridge consists of a polyethylene sheet with a supporting fabric (not shown in detail).

The filling orifice 12 may be tightly sealed with the sheathing of the metering cartridge.

The bottom 13 of the metering cartridge is tightly welded to the side wall and the gas donor 1 is located in the lower part of the cartridge. It is actuated when the activator, for example water, is filled in through the filling orifice 12.

FIG. 4 shows a continuous metering container 14, equipped with metering cartridges of the type shown in FIG. 3. In the upper part of the metering container 14 an orifice 16 is provided for the changing of the cartridge 15. A ventilation valve 17 serves to equalize the pressure in the internal space of the container 14. An inlet 18 is located in the bottom part of the container and an outlet 19 in the cover part of the container.

The cartridges 15 are surrounded after activation by the medium to be disinfected so that a quasi-continuous operation is feasible.

FIG. 5 shows a further embodiment of the invention. In the continuous metering device shown in FIG. 5, the container 20 includes flexible tube-like chambers 21 made of polyethylene, possibly with a supporting fabric. The chambers are arranged adjacent to each other and connected in series.

By means of this apparatus, the substance developing the disinfecting gas may also be passed, together with its activator, continuously through the chambers 21, so that a completely continuous operation becomes possible. The medium to be disinfected flows in through the inlet 23 and washes over all of the chambers 21, while the gas generated diffuses through the walls thereof. The gas is dissolved in the medium to be disinfected and is immediately carried off, so that diffusion through the walls of the chambers 21 is maintained uniformly continuous.

The development of gas within the chambers 21 may be controlled by the variation of the pH value. An acid activator is preferred.

By using suitable ion exchangers, the pH value may be altered in a manner known in itself, so that the reaction and the generation of gas, respectively, may be controlled.

The substance developing the disinfecting gas is introduced, together with its activator through the inlet tube 25, flows through the chambers 21 and exits through the outlet tube 26.

Figure 6:
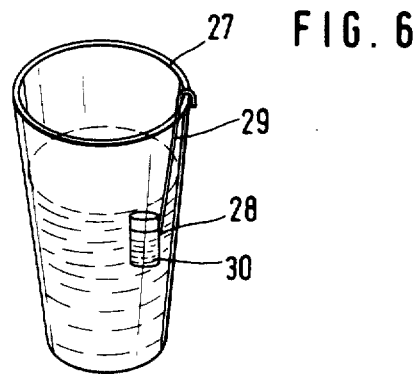
FIGS. 6 through 11 show examples of the application of the invention.

FIG. 6 shows a simple example of one application of the invention to the sterilization of small volumes of drinking water, for example, on the site where a catastrophic event has taken place. The water to be disinfected is contained in a vessel 27, wherein the cartridge 28 is immersed by means of a connecting linkage 29. The cartridge contains the clorine donor, together with its activator. The cartridge may be formed for example from a polytetrafluorethylene. Polyethylene of this type is especially resistant to chemicals so that such a cartridge has a relatively long life.

Figure 7:
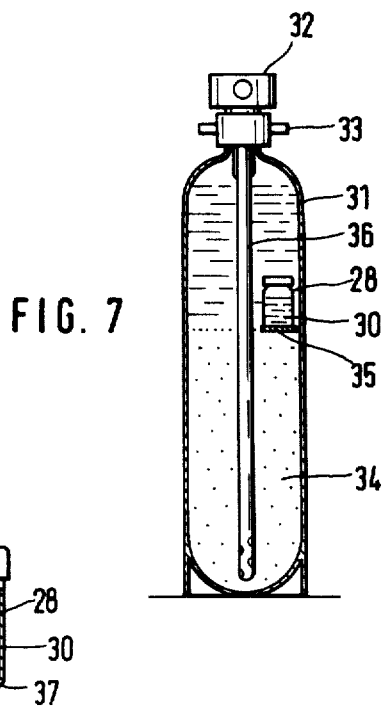

FIG. 7 shows a water softener unit having an inlet manifold 32 and outlet tube 33. The outlet is connected to a tube 36 which is equipped with a plurality of orifices. The water softener is filled to a certain height with an ion exchange resin. The tap water permeates through the ion exchange resin bed thereby loosing its hardness, rises into the tube 36, and leaves the unit at 33. The back-wash area contains a cartridge 28 filled with a chlorine donor 30 and an activator. The cartridge 30 has a ballast weight 35 so that it sinks to the surface of the ion exchange resin. The tap water contained in the back-wash area of the softener is disinfected by the cartridge 30 and after passing through the ion exchange bed, leaves the unit after being disinfected and loosing its original hardness. The water in the back-wash area has the additional effect of preventing the ion exchange resin beads from being contaminated with bacteria specially during stand-still times.

Figure 8:
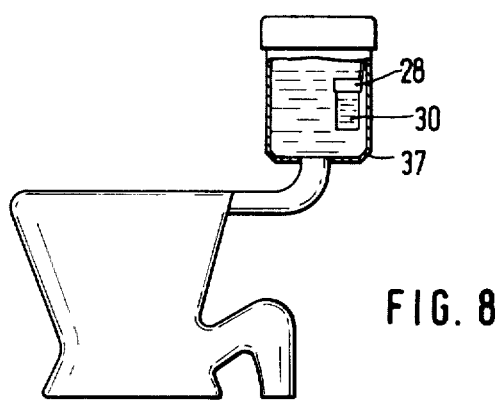

FIG. 8 illustrates another example of application. For the sterilization of sanitary facilities, a cartridge 28 made of a gas permeable synthetic material and filled with its halogen donor and the activator is placed in a toilet water tank 37. Such an arrangement is particularly advantageous in hospitals and epidemic control stations.

Figure 9:
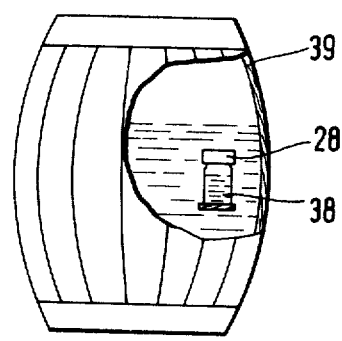

The invention is also suitable as an inhibitor of the fermentation process in yeast sterilization, for example, wooden wine barrels. Such an example is shown in FIG. 9. In this case, a cartridge 28 is filled with a donor of sulfur dioxide and an activator 38 is placed in a wine barrel 39 filled with water. For this purpose, sulfur dioxide is more suitable than chlorine, because sulfur residues potentially remaining in the barrel have no detrimental effect on the development of the wine.

Figure 10:
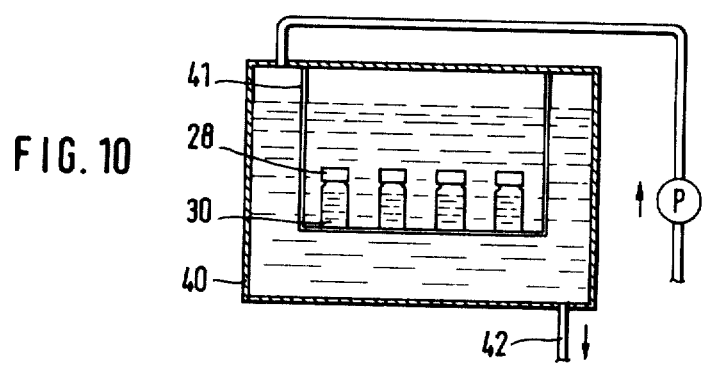

For the cleansing of bottles, milk cans, glasses and the like, it may be of advantage to have available a storage vessel with disinfecting rinsing water. An example of this is given in FIG. 10. A battery of cartridges 28 made of a gas permeable synthetic material, filled with a donor of chlorine and activator 30 is located in a storage vessel 40. The cartridges 28 are held by a support mesh 41, which may be suspended in the storage vessel 40. With the aid of a pump, the water to be disinfected is passed into the tank 40 and is discharged at 42 from the tank in a disinfected state.

Another problem consists of the storage of drinking water. Even after only a few days, algae and bacteria have multiplied in a water tank to the extent that the water was no longer potable. Following a storage period of only 5 to 8 days, a change in taste develops which continues to increase until the water becomes undrinkable. Such a problem occurs for example on ocean-going yachts not equipped with complex water treatment facilities. Further applications of this type are obvious.

Figure 11:
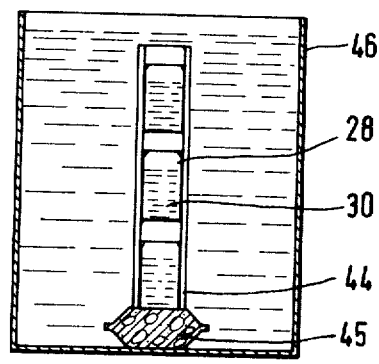

FIG. 11 presents an example of this kind, wherein a battery of cartridges 28 filled with a donor of chlorine and activator 30 is placed in a drinking water reservoir 46. The cartridges 28 are secured in their position by a frame 44, said frame being held by a heavy weight 45 on the bottom of the drinking water reservoir.

The invention provides the great advantage that substances may be used, the residues whereof have undesirable or even toxic properties. Such substances are held back by the sheet or the wall of the cartridge, so that any undesirable or toxic effect of the disinfecting agent in the human area is excluded. This allows the use of gas donors that may be produced inexpensively and which heretofore could not be employed in the human sector because of their compositions and the resulting undesirable or partially toxic effects.

What is claimed is:

1. An apparatus for the sterilization of fluids comprising:
    a substance capable of generating a disinfecting gas upon chemical activation;
    a liquid-impermeable container surrounding said substance, at least a portion of the wall of said container being formed of a solid, non-porous, liquid-impermeable synthetic plastic barrier separating said substance from a fluid to be sterilized and permitting controlled diffusion of disinfecting gas while preventing the passage of impurities and the residue of the gas generation reaction therethrough; and
    means for contacting said fluid to be sterilized with said synthetic plastic barrier.

2. The fluid sterilization apparatus of claim 1 wherein said means for contacting said fluid with said synthetic plastic barrier comprises a vessel simultaneously housing said container and said fluid.

3. The fluid sterilization apparatus of claim 1 wherein said means for contacting said fluid with said synthetic plastic barrier comprises a circuit for the flow of said fluid past said synthetic plastic barrier.

4. The fluid sterilization apparatus of claim 1 wherein said substance is activated and generates disinfecting gas upon contact with water.

5. The fluid sterilization apparatus of claim 1 wherein said container is a cartridge having at least a portion of the outside surface thereof comprised of said solid, non-porous, liquid-impermeable synthetic plastic barrier.

6. The fluid sterilization apparatus of claim 1 further comprising a plurality of said containers.

7. The fluid sterilization apparatus of claim 1 wherein said synthetic plastic barrier is formed from a solid synthetic polymer selected from the group consisting of polyethylene, polypropylene, polyvinylchloride, polyethylene-polypropyleneamide, polytetrafluoroethylene and mixtures and derivatives thereof.

8. The fluid sterilization apparatus of claim 1 wherein the disinfecting gas is selected from the group consisting of halogen, a dioxide of a halogen, sulfur dioxide and derivatives thereof.

9. The fluid sterilization apparatus of claim 1 wherein said container comprises a bag having at least a portion of the wall thereof formed of said solid, non-porous, liquid-impermeable synthetic plastic barrier.

10. The fluid sterilization apparatus of claim 1 wherein said container is a flexible tube member having at least a portion of the wall thereof covered by said solid, non-porous, liquid-impermeable synthetic plastic barrier.

11. The fluid sterilization apparatus of claim 1 wherein said container comprises two chambers separated by a releasable separating means; one of said chambers containing said substance capable of generating said disinfecting gas, and the other of said chambers containing a chemical activator for said substance.

12. The fluid sterilization apparatus of claim 1 wherein said fluid is water.

13. The fluid sterilization apparatus of claim 12 further comprising a means for introducing a chemical activator into contact with said substance capable of generating disinfecting gas.

14. The fluid sterilization apparatus of claim 13 wherein said activator introducing means comprises a conduit into said container.

* * * * *